United States Patent [19]
Haber et al.

[11] Patent Number: 4,832,680
[45] Date of Patent: May 23, 1989

[54] APPARATUS FOR HYPODERMICALLY IMPLANTING A GENITOURINARY PROSTHESIS

[75] Inventors: Terry M. Haber, Lake Forest; William H. Smedley, Lake Elsinore, both of Calif.

[73] Assignee: C.R. Bard, Inc., Murray Hill, N.J.

[21] Appl. No.: 881,829

[22] Filed: Jul. 3, 1986

[51] Int. Cl.$^4$ .............................................. A61B 19/00
[52] U.S. Cl. .................................... 600/31; 128/344; 128/DIG. 5; 623/6
[58] Field of Search ................ 128/1 R, 1.3, 343, 344, 128/DIG. 25, 129, 325; 604/49, 51, 57, 59, 60, 96, 274; 623/6

[56] References Cited

U.S. PATENT DOCUMENTS

| | | | |
|---|---|---|---|
| 2,513,014 | 6/1950 | Fields | 604/60 |
| 3,789,828 | 2/1974 | Schulte | 128/DIG. 25 |
| 3,795,246 | 3/1974 | Sturgeon | 604/99 |
| 3,834,394 | 9/1974 | Hunter et al. | 604/99 |
| 4,019,499 | 4/1977 | Fitzgerald | 128/DIG. 25 |
| 4,240,433 | 12/1980 | Bordow | 604/96 |
| 4,373,218 | 2/1983 | Schachar | 623/6 |
| 4,545,367 | 10/1985 | Tucci | 604/96 |
| 4,585,457 | 4/1986 | Kalb | 623/6 |
| 4,686,962 | 8/1987 | Haber | 128/1 R |

OTHER PUBLICATIONS

"Polytef (Teflon) Migration After Periurethal Injection: Tracer and X-Ray Microanalysis Techniques in Experimental Study", by A. A. Malizia, Jr. et al., vol. XXX, Trans. Am. Soc. Artif. Intern. Organs, 1983, pp. 330-334.

"Migration and Granulomatous Reaction After Periuretral Injection of Polytef (Teflon)", by Anthony A. Malizia, Jr. et al., vol. 251, Journal of the A.M.A., Jun. 22/29, 1984, pp. 3277-3281.

"Periurethral Polytetrafluoroethylene Injection for Uricontinent Female Subjects with Neurogenic Bladder Disease", by Robert I. Lewis et al., vol 131, Journal of Urology, Mar. 1984, pp. 459-462.

"Periurethral Polytetrafluorethylene Injection for Urinary Incontinence", by Victor A. Politano, vol. 127, Journal of Urology, Mar. 1982, pp. 439-442.

"Endoscopic Injections of Teflon to Treat Urinary Incontinence in Women", British Medical Journal, vol. 288, Jan. 21, 1984, p. 192.

Primary Examiner—Dalton L. Truluck
Attorney, Agent, or Firm—Morland C. Fischer

[57] ABSTRACT

Apparatus and a non-surgical method for hypodermically implanting a genitourinary prosthesis comprising an extensible, inflatable containment membrane to be located between the urethra and the subcutaneous corpus spongiousum of a patient to overcome urinary incontinence by means of localized, controlled tissue volume increase. Hypodermic positioning, injecting and inflating instruments are also disclosed for implant of the containment membrane and for percutaneously infusing the membrane with biocompatible fluid or particulate matter. The containment membrane functions as an envelope for retaining the fluid or particulate matter therewithin while controllably and advantageously increasing localized tissue volume and simultaneously preventing the migration of such fluid or particles. Accordingly, an increased passive occlusive pressure may be applied to the patient's urethra to achieve continence.

16 Claims, 8 Drawing Sheets

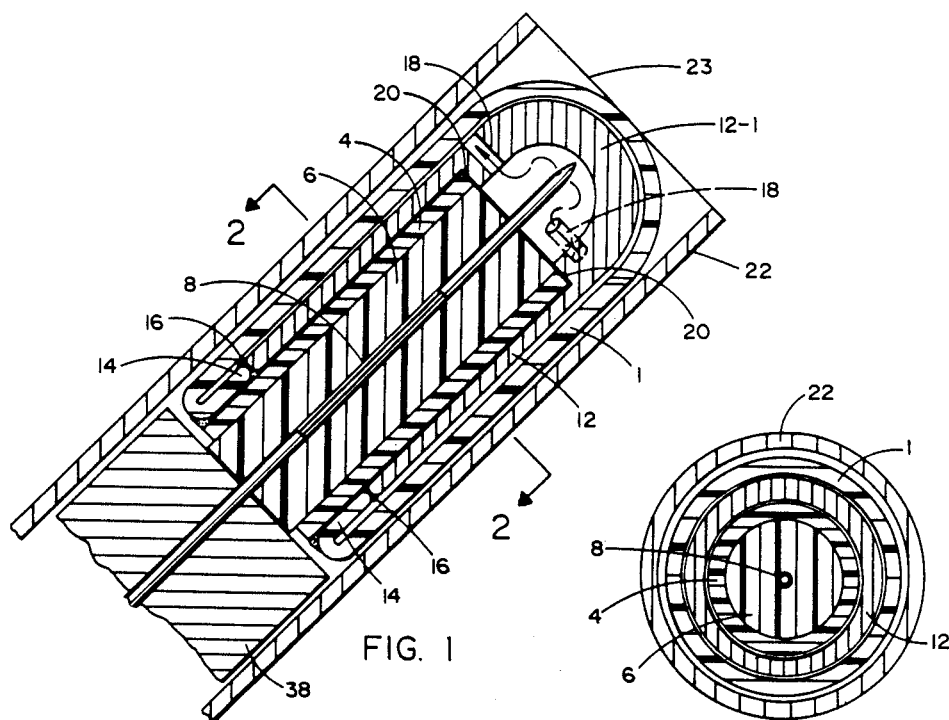
FIG. 1
FIG. 2
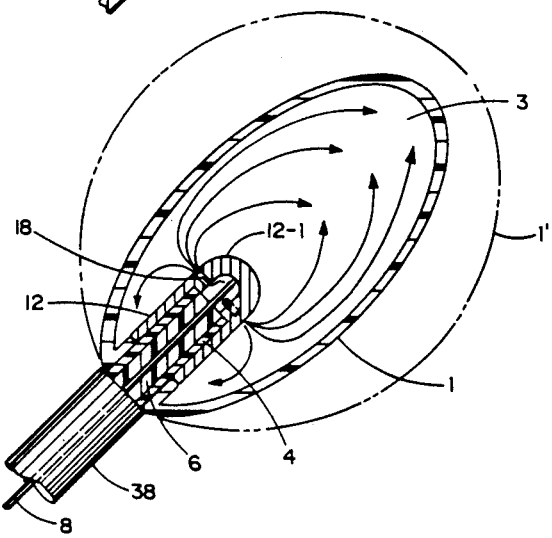
FIG. 3

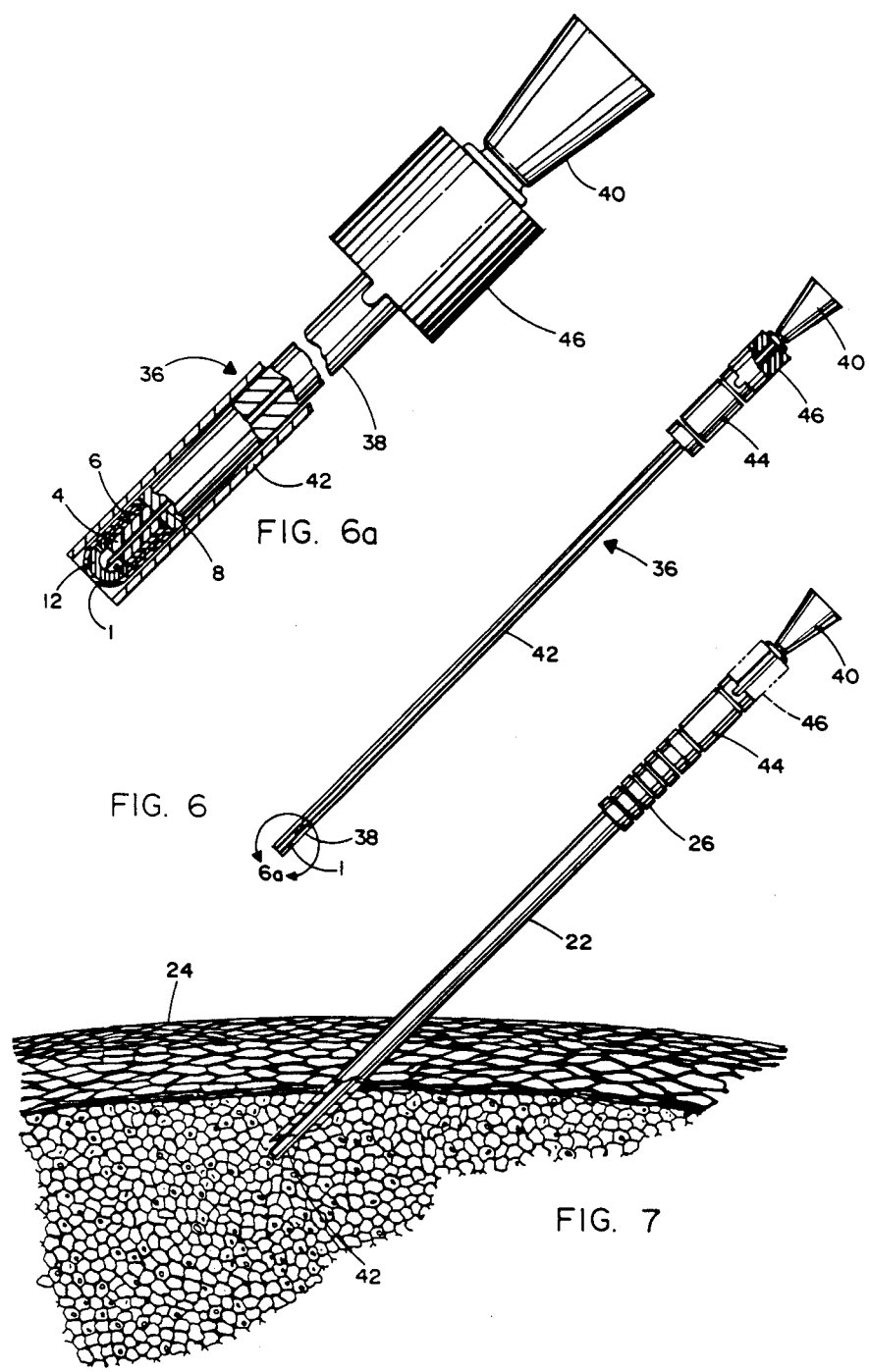

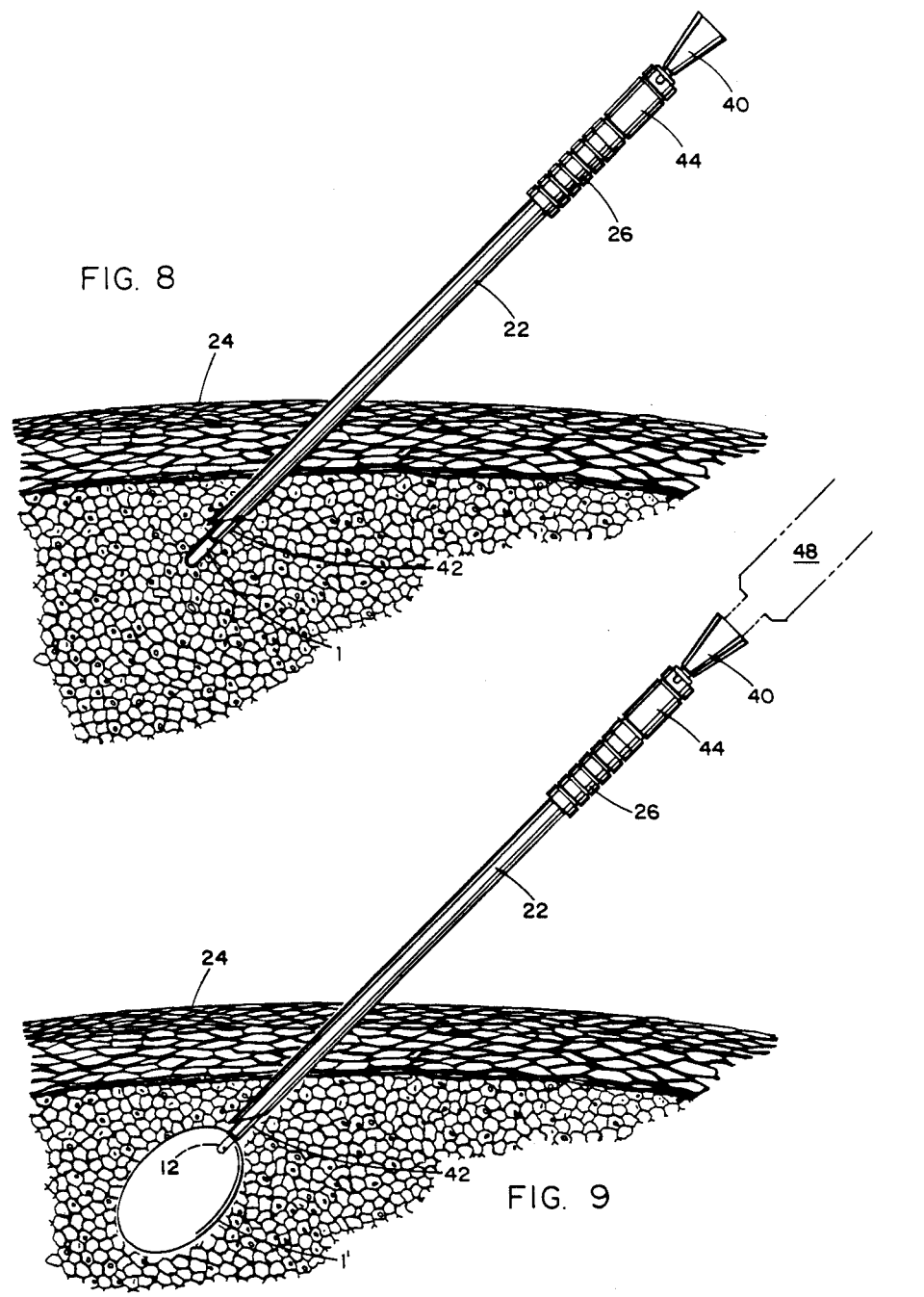

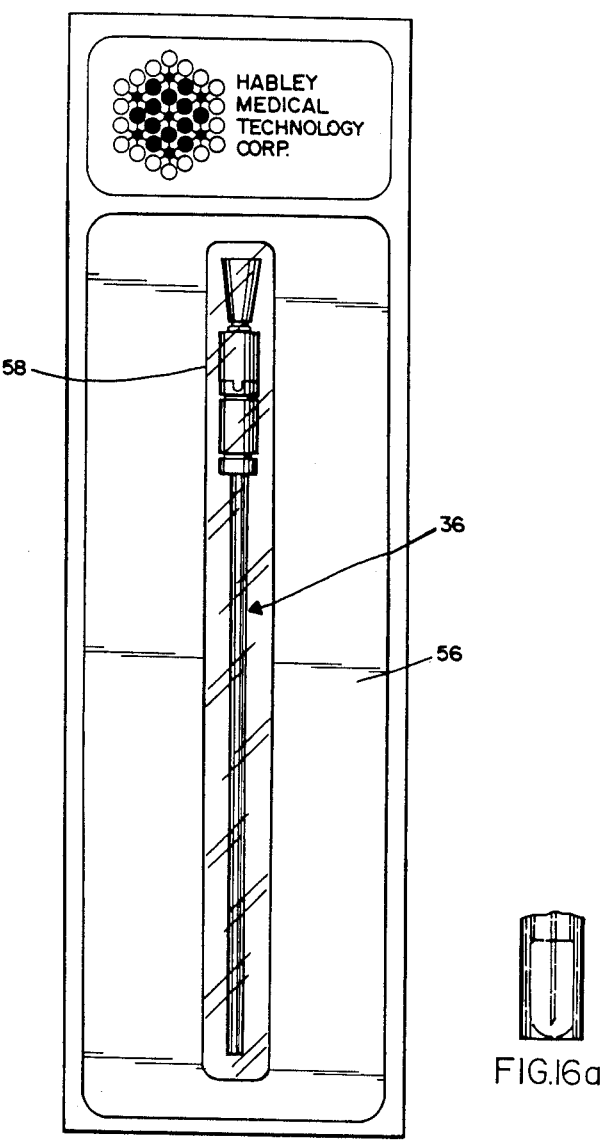
FIG. 16
FIG.16a

APPARATUS FOR HYPODERMICALLY IMPLANTING A GENITOURINARY PROSTHESIS

BACKGROUND OF THE INVENTION

1. Field of the Invention

This invention relates to an inflatable genitourinary prosthesis and to hypodermic injecting instruments for positioning, injecting and inflating the prosthesis so that increased occlusive pressure may be controllably applied to a patient's urethra for holding the patient continent. The prosthesis includes an expandable anti-migration membrane which may be percutaneously infused with fluid or particulate matter so as to increase localized tissue volume while preventing the possible migration of such fluid or particulate matter.

2. Prior Art

As will be known to those skilled in the art, in cases where the natural sphincter muscles of a patient have been surgically excised, damaged by disease or compromised by physical trauma, an artificial prosthetic sphincter has often been implanted so that occlusive pressure may be applied to the urethra to restore continence. Artificial sphincters are well-known and specific examples thereof will not be listed. However, the implantation of an artificial sphincter commonly requires a surgical procedure which necessitates the hospitalization of the patient. Such a procedure is relatively complex and expensive, and usually requires six to eight weeks or more of recovery time. Accordingly, both the patient and his physician face approximately two months delay before actuation of the prosthesis and being able to ascertain whether the surgery has been successful and the implant is functioning. More particularly, because of the swollen and aggravated condition of edema of the urethral tissues during and for a period subsequent to surgery, the physician cannot precisely match the occlusive pressure to the patient's urethra. Therefore, the physician must estimate the required minimal occlusive pressure needed to achieve coaptation in that particular patient. As a consequence of such estimate, sphincteric mechanisms are often improperly selected or fitted, so that the occlusive pressures generated by such mechanisms are either insufficient to successfully achieve continence or excessive to the point of causing ischemia and subsequent erosion of urethral tissue. Excessive occlusive forces may undesirably minimize arteriovascular blood flow to the urethra and thereby cause ischemia and subsequent erosion of the delicate tissues. What is more, if the implant surgery should prove to be unsuccessful (i.e. the maximum occlusive pressure to be generated by the sphincter is insufficient to hold the patient continent or the sphincter malfunctions mechanically), then additional surgery becomes necessary to provide sphincter adjustment, repair or explant.

In the recent past, it has been suggested that urinary incontinence may be successfully treated by non-surgical means with the periurethral injection of TEFLON paste to increase localized tissue volume and thereby increase the available occlusive pressure to be applied to the urethra of an incontinent patient. However, certain problems have been encountered as a consequence of the migration of the paste from the injection site. That is, such paste has been known to induce tissue reaction and form TEFLON-induced granulomas in certain individuals. Because of the possible toxicity of TEFLON-based paste, concern for patient safety has also been expressed. Hence, an otherwise advantageous, non-surgical procedure has now experienced some disfavor, and reduced application.

SUMMARY OF THE INVENTION

Briefly, and in general terms, this invention relates to a non-surgical procedure for successfully treating urinary incontinence. More particularly, a unique genitourinary prosthesis comprising an extensible and inflatable elliptoidal or pyriform-shaped membrane is provided to be periurethrally injected to form an enclosure for receiving and containing a supply of fluid or particulate matter. In this manner, the membrane is precisely and controllably inflated while in situ so as to apply increased localized tissue volume and proportionately greater occlusive pressure to the urethra to restore the patient's continence. However, the previous problem of particle migration is solved by virtue of the anti-migration membrane in which the fluid or particulate matter are retained.

The genitourinary prosthesis of this invention is implanted by means of specialized hypodermic positioning, injecting and inflating instruments and instrumentation. The instruments include an outer trocar tube to dilate a suitably sized insertion channel through the targeted patient tissues. Located within the outer tube is the containment membrane in an uninflated state. A needle extends through a stylus also located within the outer tube for placing the interior of the containment membrane in communication with a source of supply of fluid or particulate matter. With the containment membrane suitably implanted at the bulbar urethra, the membrane is percutaneously infused with a measured supply of fluid or particulate matter via the needle, whereby to inflate the membrane. An inflation of the membrane proportionately increases local tissue volume in the area of the corpus spongiousum to correspondingly increase the occlusive pressure applied to the urethral tissues for restoring a patient's continence. The positioning, injecting and inflating instrumentation is withdrawn from the urethral tissue leaving the inflated containment membrane to form an envelope for preventing the undesirable migration of the fluid or particulate matter. One or more of the genitourinary prostheses of the present invention may be implanted, as just described, depending upon etiology, residual sphincteric function, vascularity and physical properties of that individual patient's tissues.

BRIEF DESCRIPTION OF THE DRAWINGS

FIG. 1 is a cross-section of the genitourinary prosthesis of the present invention showing a containment membrane in an uninflated state;

FIG. 2 is a cross-section taken along lines 2—2 of FIG. 1;

FIG. 3 shows the containment membrane of FIG. 1 in an injected, inflated state;

FIGS. 4-12 illustrate the method and instruments of the present invention for positioning, injecting and inflating the containment membrane below the urethral tissue of an incontinent patient;

FIG. 16 shows a package for retaining certain disposable components of the implant instruments of FIGS. 4–12 in a sterile, ready-to-use environment.

FIG. 16a shows a detail of the package of FIG. 16.

DESCRIPTION OF THE PREFERRED EMBODIMENT

Figure 4:
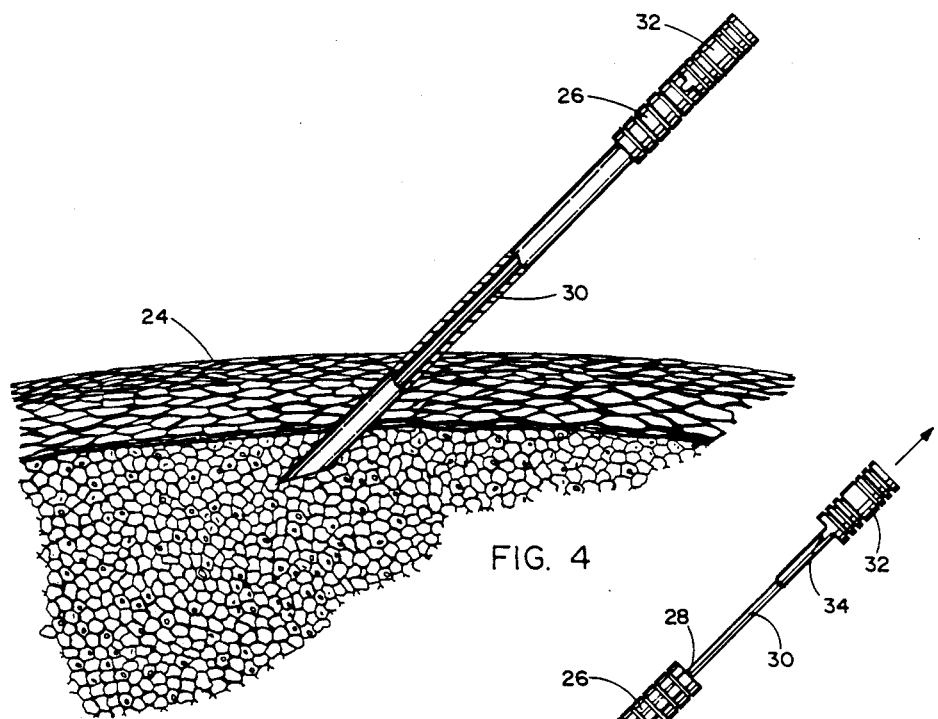

The structure of the presently disclosed hypodermically implantable genitourinary prosthesis and the instruments to implant and inject such prosthesis are now described while referring initially to FIGS. 1–3 of the drawings. FIG. 1 shows the prosthesis in an unexpanded state and FIG. 3 shows the prosthesis in an injected and (partially) expanded state. The genitourinary prosthesis of the present invention comprises an elastomeric, elliptoidally-shaped containment membrane 1 which, in the pre-injection state of FIG. 1, is unfilled (i.e. devoid of particles and fluid). The containment membrane 1 is preferably formed from a suitable tear-resistant, biocompatible material, such as, for example, polyurethane, silicone, latex, or the like.

Located at the entrance to containment membrane 1 is a valve assembly including a cylindrical compression band 4 which surrounds a valve core 6 of solid cross-section. Each of the compression band 4 and valve core 6 is preferably formed from a high memory, elastomeric polymer such as, for example, silicone, or the like, and the material of valve core 6 is also characterized by a relatively low durometer. In the assembled relationship, the compression band 4 pre-stresses the valve core 6 to increase the functional density thereof to promote an efficient self-healing of any wound formed therein. Extending through the solid core 6 and being supported thereby in concentric alignment with compression band 4 (best illustrated in FIG. 2) is a Whitacre-type hypodermic needle 8. Needle 8 projects outwardly from a stylus 38 and terminates at the evacuated interior 3 of containment membrane 1. As will be explained in greater detail hereinafter when referring to FIG. 9, the needle 8 permits a measured supply of fluid or particulate matter to be percutaneously infused to the interior 3 of membrane 1 to inflate the prosthesis (designated 1' in the expanded state of FIG. 3).

Located between containment membrane 1 and compression band 4 is a tubular needle stop 12 having a hemispheric first end 12-1 and an open opposite end 12-2. The needle stop 12 is preferably formed from a suitable structurally sound, biocompatible, radio opaque and corrosion-resistant biomaterial such as, for example, titanium, or the like. The open end of the needle stop 12-2 is interconnected with the corresponding open end of the elliptoidally-shaped containment membrane 1. More particularly, the open end of the containment membrane 1 is turned back upon itself to form a U-shaped connecting terminal 14. Connecting terminal 14 is aligned with and connected to the open end of the needle stop 12 by means of a suitable polymeric adhesive 16, such as silicone, or the like.

In the assembled relationship of FIG. 1, the needle stop 12 performs multiple functions. That is, metallic hemispheric end 12-1 provides a stop to limit the forward movement of needle 8 towards containment membrane 1. Hence, needle stop 12 prevents the needle 8 from accidentally penetrating the containment membrane 1 and thereby avoids the possibility of leaking migratory fluid or particulate matter into the patient's body, a problem which is otherwise common to other non-surgical medical attempts to overcome incontinence. The hemispheric end 12-1 is also provided with a suitable number of delivery ports 18 extending therethrough. Such delivery ports permit communication between the needle 8 and the interior 3 of containment membrane 1 (best represented in FIG. 3) during the inflation of the membrane by suspended particulate matter or fluid in a manner which will soon be described. The hemispheric end 12-1 of needle stop 12 terminates at a shoulder 20. The compression band 4 and core 6 are received against the shoulder of needle stop 12 so as to limit any forward movement of such band or core towards hemispheric end 12-1 and thereby avoid a possible blockage of delivery ports 18.

The present prosthesis is surrounded by a hollow, cylindrical outer trocar tube 22. Trocar tube 22 is formed of a biocompatible and corrosion-resistant material, such as titanium, or the like, and functions, in part, as a removable outer casing to protect the integrity of and to guide the containment membrane during implantation. Trocar tube 22 also functions as an instrument by which to penetrate the urethral tissues of the patient to establish a suitable channel therethrough so that the prosthesis may be implanted within the bulbar urethra of the corpus spongiousum (best shown in FIG. 13b). To this end, trocar tube 22 is provided with a sharp, oblique cutting surface 23 for establishing a suitably sized passage through the urethral tissue through which to insert the prosthesis.

Figure 5:
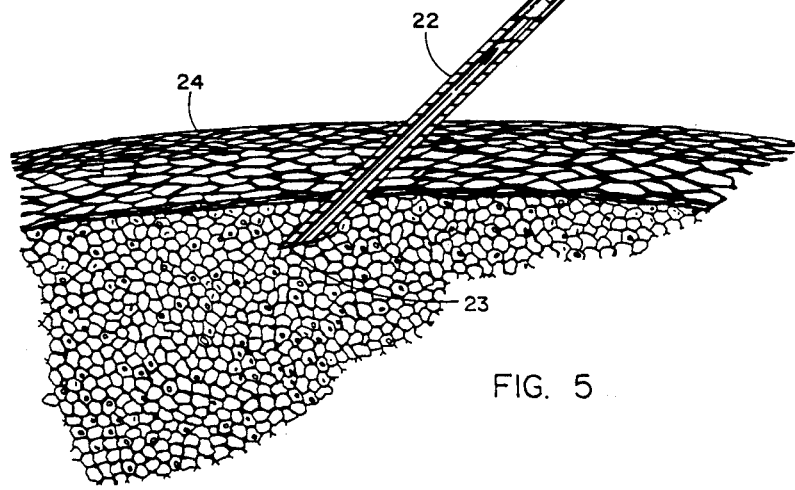

Referring now to FIGS. 4 and 5 of the drawings, the trocar tube 22 is shown penetrating the urethral tissue 24. Located opposite oblique cutting surface 23 is a knurled gripping portion 26 at which the physician may apply the force necessary to insert or remove trocar tube 22. A small notch 28 or keyway is formed in gripping portion 26. Prior to the step of penetrating the urethral tissue 24, a non-coring trocar rod 30 of solid cross-section is inserted into, and completely through, the hollow outer trocar tube 22. Inner trocar rod 30 is formed of stainless steel, or the like, and has a closed oblique end opposite a knurled gripping portion 32 at which the physician may insert or remove rod 30. Extending from gripping portion 32 is a key 34 which is particularly sized to be received within keyway 28. That is, the inner rod 30 may be rotated (by means of gripping portion 32) and the key 34 thereof located in the keyway 28 of trocar tube 22 to form an interlock therebetween and thereby preserve an alignment of the respective oblique trocar ends relative to one another (best shown in FIG. 4). The presence of non-coring inner rod 30 within outer tube 22 prevents the patient's tissues from entering the outer tube 22 during such time as when the trocar is used to penetrate the urethral tissue 24. Hence, trauma will be minimal because none of the patient's tissues will be removed with the outer trocar tube 22 at the conclusion of the soon to be described process for implanting the prosthesis. Once a suitable channel has been pierced such that outer trocar tube 22 has penetrated the patient's urethral tissue to a desired subcutaneous position within the corpus spongiousum, the inner trocar rod 30 is withdrawn from outer tube 22 (best illustrated in FIG. 5).

In FIGS. 6-8 of the drawings, a casing and positioning cartridge 36 is described for moving the prosthesis of this invention through trocar tube 22 and precisely locating the prosthesis within the tissues of the corpus spongiousum. Referring initially to FIGS. 6 and 6a, the casing and positioning cartridge 36 includes a hypodermic stylus 38. At one end of stylus 38 is a conventional luer lock 40. Extending outwardly from the opposite end of stylus 38 is the needle 8 being surrounded by the valve core 4, compression band 6, needle stop 12 and containment membrane 1 (best shown in FIG. 6a and previously described in detail when referring to FIG. 1). As will soon be explained, luer lock 40 provides a convenient injection port for placing the tip of a hypodermic syringe (not shown) into communication with the containment membrane 1 by way of the needle 8 which extends through the body of stylus 38 to luer lock 40. Casing and positioning cartridge 36 also includes a hollow outer cylinder 42 into which the stylus 38 is inserted for the pre-injection protection of membrane 1. One end of outer cylinder 42 is open to permit the needle-carrying end of stylus 38 to be moved outwardly therefrom for the purpose of inflating containment membrane 1 (as best illustrated in FIG. 9). The opposite end of outer cylinder 42 is provided with a gripping portion 44 so that the physician can reliably handle cylinder 42.

In the casing and positioning cartridge 36 of FIG. 6, the stylus 38 is shown inserted through the outer protective cylinder 42. However, a removable and disposable compression resistant collar 46 is also shown located between the gripping portion 44 of cylinder 42 and the luer lock 40 of stylus 38. Collar 46 functions as a spacer during the packaging and transport of the casing and positioning cartridge 36, such that the luer lock 40 is held above gripping portion 44 and the containment membrane 1 is withdrawn slightly into the open end of outer cylinder 42.

As was previously disclosed while referring to FIGS. 4 and 5, the outer trocar tube 22 first penetrates a patient's urethral tissue (in FIG. 4), and a non-coring inner trocar rod 30 is then removed therefrom (in FIG. 5). Next, and referring now to FIG. 7 of the drawings, the prosthesis casing and positioning cartridge 36, including stylus 38 placed within outer cylinder 42, is inserted into and through the interior of trocar tube 22. Accordingly, the gripping portion 44 of outer cylinder 42 is positioned adjacent the gripping portion 26 of trocar tube 22, such that the open end of cylinder 42 extends slightly outward from the trocar cutting surface. The collar 46 (now shown in phantom) is removed from stylus 42 and discarded. The physician then depresses the luer lock end of stylus 38 so as to slide the stylus 38 downwardly through the outer cylinder 42. Accordingly, and as is best shown in FIG. 8 of the drawings, luer lock 40 is moved into position adjacent gripping portion 44 and the containment membrane 1 is moved through the open end of outer cylinder 42.

In FIG. 9 of the drawings, a high pressure hypodermic syringe 48 (shown in phantom) is interconnected with luer lock 40 at the proximal end of stylus 38. Syringe 48 contains a measured supply of fluid or suspended particulate matter, a regulated amount of which is percutaneously infused to the interior of containment membrane 1 via the needle 8 (in FIG. 1) which passes through stylus 38. The membrane is thereby inflated according to the tissue requirements of the patient to increase both the localized tissue volume and the passive occlusive pressure to restore a patient's urinary continence. By way of example, the syringe 48 may be filled with suspended TEFLON particles, spheres, radio opaque isotonic fluid, isotonic saline solution, and the like, although the particular material selected is not to be regarded as a limitation of this invention. Moreover, the ellipsoidally-shaped containment membrane 1' serves as a non-permeable envelope for preventing the migration of the fluid or suspended particulate matter. What is more, the containment membrane 1' may be precisely and controllably infused with the minimum volume of liquid or solid particle suspension necessary to achieve coaptive continence of the urethral tissue whereby to reduce the possibility of impeding the blood flow through the patient's urethra as a consequence of ischemia. The containment membrane 1' may have an associated loop 49 to enable the removal or displacement thereof.

Figure 10:
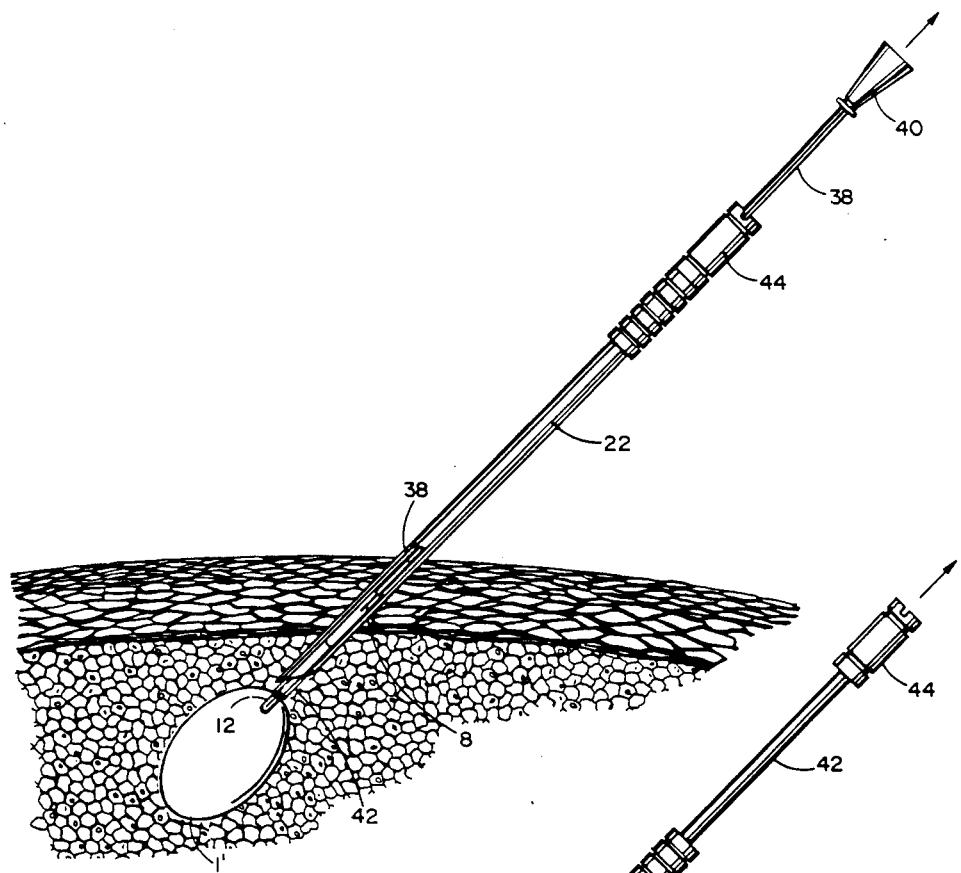

After the containment membrane 1' has been suitably positioned and inflated, the implant and injection instruments for accomplishing the foregoing are removed from the patient's body. That is, referring concurrently to FIGS. 10-12 of the drawings, the physician grasps the stylus 38 at the luer lock 40 thereof and exerts an upward pulling force to withdraw stylus 38 from the interior of outer cylinder 42 (best illustrated in FIG. 10). The withdrawal of stylus 38 correspondingly removes the needle 8 from the needle stop 12 at the interior of inflated containment membrane 1'. However, and as previously disclosed, the solid valve core 6 (of FIG. 1) which is held in a state of compression by compression band 4 (also of FIG. 1) immediately heals any possible leakage channel that may have been created by the prolonged presence of and post-implant removal of needle 8, such that a fluid-tight seal is formed to prevent the deflation of membrane 1' and the escape of fluid or suspended particles. The cavity produced by inflation of the containment membrane within the patient's tissue produces a locating effect which prevents the inflated membrane 1' from being pulled with stylus 38 at such time as when the stylus is withdrawn from cylinder 42.

Figure 11:
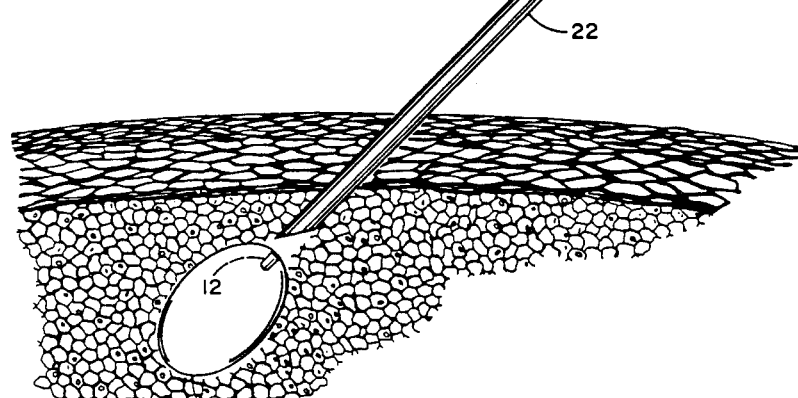
Figure 12:
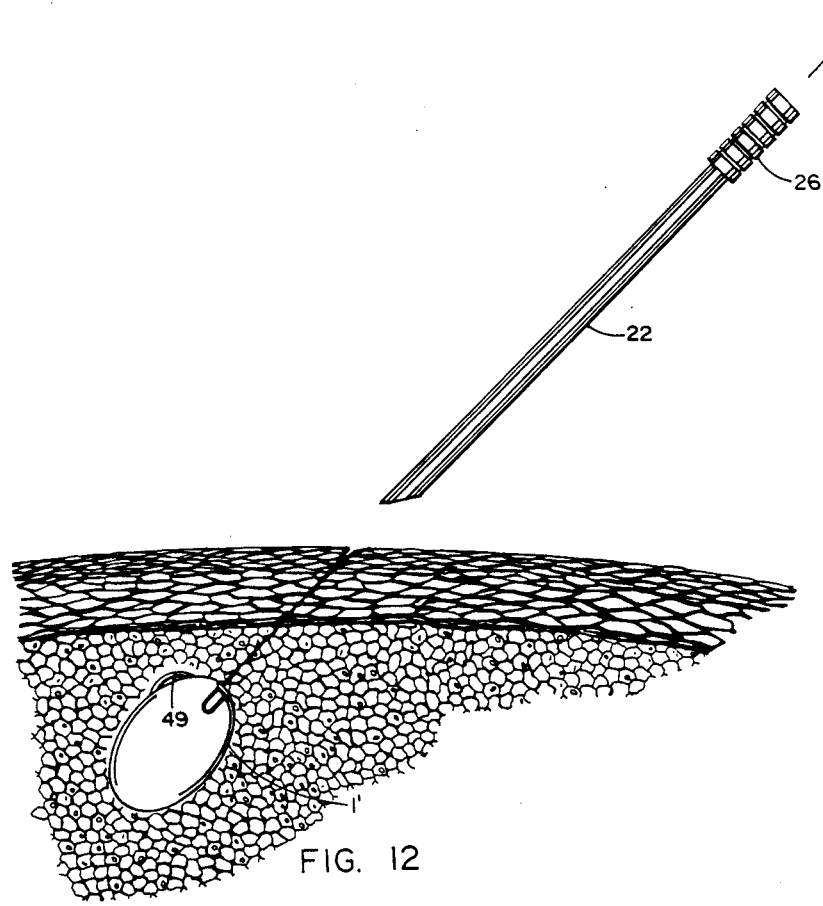

Next, the physician grasps the outer stylus cylinder 42 at the gripping portion 44 thereof and exerts an outwardly pulling force to withdraw outer cylinder 42 from the interior of trocar tube 22 (best illustrated in FIG. 11). The prosthesis casing and positioning cartridge (designated 36 in FIG. 6) comprising both the stylus 38 and the outer stylus cylinder 42 may be disposed of after removal from the trocar tube 22. Lastly, the physician grasps the trocar tube 22 at the gripping portion 26 thereof and exerts an outward pulling force to withdraw trocar tube 22 from the patient's body (best illustrated in FIG. 12) thereby leaving behind a relatively minor puncture wound. Thus, as an important advantage of this invention, the patient will require a substantially shorter recovery time or no recovery time at all as compared to approximately two months or more if a conventional prosthetic sphincter had been surgically implanted as a hospital in-patient. Moreover, the high cost, confinement and inconvenience commonly associated with such a hospital procedure can be eliminated, since the implant can be injected under a local anesthetic and treated on an out-patient basis.

Figure 13A:
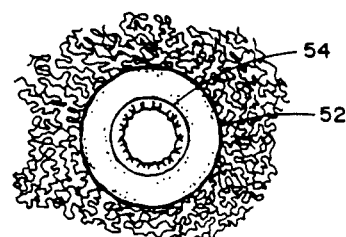
FIGS. 13a and 13b show a lateral section of the patient's corpus spongiousum and urethra in relaxed and occluded conditions, respectively, and the preferred location of the containment membrane for the treatment of urinary incontinence.
Figure 13B:
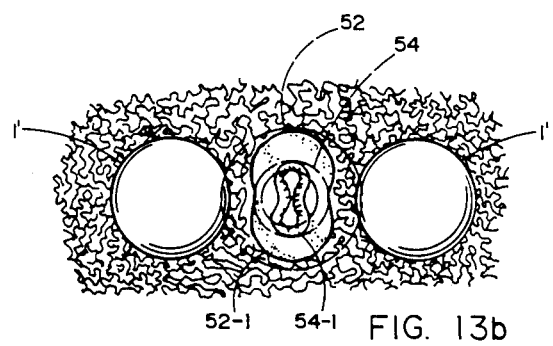

FIG. 13a of the drawings represents the non-expanded corpus spongiousum 52 and non-occluded urethral tissue 54 of an incontinent patient prior to the implantation of the genitourinary prosthesis of this invention. FIG. 13b of the drawings represents a volume increase of the corpus spongiousum 51 and an occluded urethra 54-1 of a patient who is now restored to urinary continence after the present prosthesis has been suitably implanted to expand the corpus spongiousum and thereby occlude the urethra (non-expanded corpus spongiousum and the non-coapted urethra of an incontinent patient being shown for comparison purposes in phantom and represented by the previously used reference numerals 52 and 54, respectively).

Although the presently disclosed invention has been explained with reference to a single, implantable genitourinary prosthesis 1', it is to be expressly understood that any number of such prostheses may be implanted, depending upon the increased tissue volume and resulting occlusive pressure which is required to permit the patient to be restored to continence. That is, after one or more prostheses have been implanted, the physician may monitor the patient's degree of continence. In the event that greater occlusive pressure is needed, the physician may implant a corresponding additional number of prostheses until patient continence is restored. In the example of FIG. 13b, a pair of inflated prostheses 1' are oppositely disposed relative to one another within the subcutaneous corpus spongiousum 52. In this manner, diametric occlusive pressure may be applied to the urethral tissue to restore the patient to a continent condition.

Referring briefly to FIGS. 16 and 16a of the drawings, a packaging arrangement is shown by which the prostheses casing and positioning cartridge 36 (best described when referring earlier in FIG. 6) may be transported in a sterile manner, safely stored and inventoried. By way of example, a cartridge 36 is placed on a backing 56 and then covered by a transparent plastic bubble 58 to form a hermetically sealed environment. The cartridge assembly is then sterilized by irradiation or other means. Because of its disposable nature, the physician may wish to retain a number of casing and positioning cartridge packages, so that one or more of the sterile casing and positioning cartridge assemblies 36 will be readily available for use by the physician to perform the procedure as hereinabove described.

Figure 14:
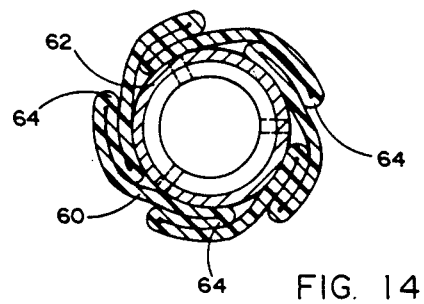
FIG. 14 shows an alternate folded geometry for the containment membrane of FIG. 1 in the uninflated condition.
Figure 15:
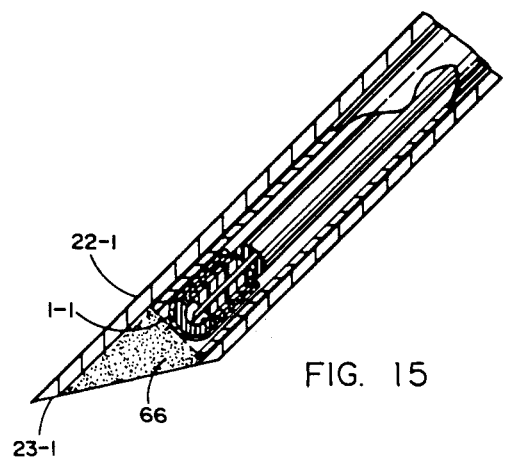
FIG. 15 shows alternate instruments for positioning, injecting and inflating the containment membrane of FIG. 1.

FIGS. 14 and 15 of the drawings illustrate modifications of the present invention. In FIG. 14, a folded containment membrane 60 is shown around a needle stop 62 in the preinjected and unexpanded state (similar to FIG. 1). That is, the membrane 60 may contain a plurality of folds 64 around the periphery thereof to increase the surface area and resulting volumetric capacity at such time when the membrane is injected and expanded (similar to FIG. 3). Accordingly, the containment member 60 may be inflated to a larger volume in cases where increased occlusive pressure must be generated to enable a patient's continence to be restored.

In FIG. 15, a modified instrument is shown whereby use of the non-coring, inner trocar rod (designated 30 in FIGS. 4 and 5) is eliminated. More particularly, a mass of bioabsorbable polymer material 66 is placed within the outer trocar tube 22-1 between the oblique cutting end 23-1 thereof and the ellipsoidally-shaped containment membrane 1-1. By way of example, material 66 may be polyglycolic acid (PGA) having a controllable rate of disintegration. In operation, material 66 acts as a fairing across cutting end 23-1 and thereby performs a non-coring function when the outer trocar tube 22-1 penetrates the patient's urethral tissue to form a puncture wound through which to implant membrane 1-1. Upon withdrawal of the trocar tube 22-1, the material 66 is left behind to disintegrate and eventually to be absorbed by the patient's tissues. By virtue of the modification of FIG. 15, a single, self-contained instrument package is available for making a suitable puncture and for packaging, positioning and inflating the prosthesis of this invention.

It will be apparent that while a preferred embodiment of the invention has been shown and described, various modifications and changes may be made without departing from the true spirit and scope of the invention. For example, the containment membrane has applications other than as an injectable prothesis for enabling a patient to overcome incontinence. More particularly, the envelope can be formed from a selectively permeable (by a gas or liquid) membrane which can be implanted as a drug delivery system. Other applications include that of a variable volume mass to replace surgically removed tissue and/or organ excisions or as an injectable anti-ureteral reflux mass. Still further applications of the present invention include a testicular prothesis, injectable prosthetic eye, prosthetic sphincter and injectable intraocular lens. Of course, the prosthesis of this invention is also applicable for controllably occluding luminal passages other than the patient's urethra when it is necessary to selectively control the flow of material therethrough.

Having thus set forth a preferred embodiment, what is claimed is:

1. Apparatus for treating urinary incontinence and comprising:

an inflatable containment membrane being in a normally uninflated condition;

outer tube means having a cutting end for puncturing the urethral tissues of a patient undergoing treatment, said containment membrane being located within said outer tube means;

stylus tube means located within and movable relative to said outer tube means for urging said containment membrane outwardly from the cutting end thereof and for positioning said containment membrane proximally to the patient's urethra, one end of said stylus tube means being interfaced with a source of material;

a hollow needle connected to the opposite end of said stylus tube means and communicating with the interior of said containment membrane such that said containment membrane is detachably carried by said needle, said containment membrane being percutaneously infused with and inflated by a supply of material from the source thereof by way of said stylus tube means and said needle to increase local tissue volume and the occlusive pressure applied to the urethra for holding the patient continent; and protective cylinder means located within and slidable through said outer tube means, said stylus tube means located within and slidable through said protective cylinder means so that the containment membrane being carried by said needle will be positioned within and protected by said cylinder means.

2. The apparatus recited in claim 1, further comprising a needle stop located between the material delivering end of said needle and said containment membrane to prevent the accidental puncture of said membrane by said needle, said needle stop having at least one opening formed therethrough to permit the delivery of material from said needle to the interior of said membrane.

3. The apparatus recited in claim 1, further comprising plug means located in an open end of said containment membrane, said needle being removably inserted through and releasably retained by said plug means so that material can be delivered to the interior of said containment membrane, said plug means forming a fluid-tight closure at the open end of said membrane to prevent the escape of material when said membrane has been inflated and said needle has been removed.

4. The apparatus recited in claim 3, further comprising compression band means extending around said plug means to maintain said plug means in a state of compression for sealing a puncture channel when said needle is removed therefrom.

5. The apparatus recited in claim 1, further comprising non-coring means associated with said outer tube means to prevent the patient's tissue from entering said outer tube means when said tube means pierces the urethral tissues, said non-coring means comprising inner tube means having a closed end, said inner tube means being slidable through said outer tube means until the closed end thereof is aligned with the cutting end of said outer tube means when said puncture is made, said inner tube means being removed from said outer tube means after said outer tube means penetrates the patient's urethral tissues and a puncture is made.

6. The apparatus recited in claim 1, further comprising spacer means removably positioned between said stylus tube means and said protective cylinder means, the presence of said spacer means preventing the slidable movement of said stylus tube means through said cylinder means and fixing the position of said tube means relative to said cylinder means, such that the needle carrying end of said stylus tube means is located within and protected by said protective cylinder means.

7. Apparatus for treating urinary incontinence and comprising:
an inflatable containment membrane being in a normally uninflated condition;
outer tube means having a cutting end for puncturing the urethral tissues of a patient undergoing treatment, said containment membrane being located within said outer tube means;
positioning means carried by said outer tube means for urging said containment membrane outwardly from the cutting end thereof and for positioning said containment membrane proximally to the patient's urethra;
hollow passage means extending through said outer tube means and communicating between the interior of said containment membrane and a source of material, said containment membrane being percutaneously infused with and inflated by a supply of the material by way of said passage means to increase local tissue volume and the occlusive pressure applied to the urethra for holding the patient continent; and
non-coring means associated with said outer tube means to prevent the patient's tissue from entering said outer tube means when said tube means pierces the urethral tissues, said non-coring means including a bioabsorbable fairing located in said outer tube means between the cutting end thereof and said containment membrane.

8. Apparatus for treating urinary incontinence and comprising:
an inflatable containment membrane being in a normally uninflated condition;
outer tube means having a cutting end for puncturing the urethral tissues of a patient undergoing treatment, said containment membrane being located within said outer tube means;
positioning means carried by said outer tube means for urging said containment membrane outwardly from the cutting end thereof and for positioning said containment membrane proximally to the patient's urethra;
hollow passage means extending through said outer tube means and communicating between the interior of said containment membrane and a source of material, said containment membrane being percutaneously infused with and inflated by a supply of the material by way of said passage means to increase local tissue volume and the occlusive pressure applied to the urethra for holding the patient continent;
non-coring means associated with said outer tube means to prevent the patient's tissue from entering said outer tube means when said tube means pierces the urethral tissues, said non-coring means including a bioabsorbable fairing located in said outer tube means between the cutting end thereof and said containment membrane,
said bioabsorbable fairing being formed from material including polyglycolic acid.

9. A non-surgical method for perineal injection of a prosthesis comprising an inflatable containment membrane for increasing the occlusive pressure applied to a patient's urethra for treating urinary incontinence, said method comprising the steps of:
piercing a small tunnel through the patient's urethral tissues with a hollow piercing instrument;
locating a protective cylinder within and sliding said protective cylinder completely through said hollow piercing instrument;
detachably connecting an uninflated containment membrane to one end of a hollow needle and interconnecting the opposite end of said needle with a source of material;
locating said needle within and sliding said needle through said protective cylinder so that the uninflated containment membrane connected to said needle will be protected within said cylinder and moved outwardly from said piercing instrument so as to be located relative to the patient's urethra;
percutaneously infusing said containment membrane with material from the source thereof by way of said needle to inflate said membrane and thereby increase the occlusive pressure applied to the urethra;
detaching said inflated containment membrane from said needle; and
removing said needle from said protective cylinder, said protective cylinder from said piercing instrument, and said piercing instrument from the punctured urethral tissues.

10. The method recited in claim 9, including the additional steps of inserting a non-coring rod into said hollow piercing instrument at the time that said tunnel is cut to prevent the patient's tissue from entering said piercing instrument; and
removing said non-coring rod before said containment membrane is located at the interior of said piercing instrument.

11. A genitourinary prosthesis for treating urinary incontinence, said prosthesis comprising an extensible, inflatable containment membrane to be implanted in an uninflated condition within the body of a patient so as to be inflated while in situ, said containment membrane including valve means through which a hypodermic needle may be inserted to place the interior of said containment membrane in communication with a source of material to inflate said membrane with material from said source, said membrane serving as an envelope in the inflated condition to increase local tissue volume proximally to the patient's urethra and prevent the migration of the material from said membrane, and said valve means including a needle stop being arranged in spaced axial alignment for engaging said hypodermic needle to limit the insertion of said needle through said valve means and thereby prevent the accidental puncture of said containment membrane by said needle, said needle stop having at least one opening located between said needle and said containment membrane to permit material to be delivered from said needle to the interior of said membrane via said opening.

12. The prosthesis recited in claim 11, further comprising compression band means extending around said valve means to maintain said valve means material in a state of compression for sealing a puncture channel when the hypodermic needle is removed from said valve means after inflation of said containment membrane.

13. The non-surgical method recited in claim 19, including the additional steps of forming plug means at an open end of said containment membrane to form a fluid-tight closure of said open end for preventing the escape of material therefrom after said membrane has been infused, inserting said needle through said plug means and into the interior of said membrane, and locating a needle stop between said plug means and said membrane to prevent the accidental puncture of said membrane by said needle.

14. The non-surgical method recited in claim 19, including the additional steps of positioning said containment membrane relative to the patient's urethra by means of a hollow stylus tube, connecting said needle to one end of said stylus tube, interconnecting the opposite end of said stylus tube to the source of material, and infusing said membrane with material from said source via said stylus tube and said needle.

15. The non-surgical method recited in claim 19, including the additional step of moving said stylus tube through the interior of said protective cylinder for sliding said containment membrane outwardly from said piercing instrument and for positioning said membrane relative to the patient's urethra.

16. The genitourinary prosthesis recited in claim 11, wherein the needle stop of said valve means is located between said containment membrane and the end of said valve means from which said needle emerges to communicate with the interior of said membrane, said needle stop intercepting said needle prior to contact with said membrane.

* * * * *

UNITED STATES PATENT AND TRADEMARK OFFICE
CERTIFICATE OF CORRECTION

PATENT NO. : 4,832,680
DATED : May 23, 1989
INVENTOR(S) : Terry M. Haber et al

It is certified that error appears in the above—identified patent and that said Letters Patent is hereby corrected as shown below:

Claim 13, line 1, change "19" to --9--.

Claim 14, line 1, change "19" to --9--.

Claim 15, line 1, change "19" to --14--.

Signed and Sealed this

Twenty-second Day of May, 1990

Attest:

HARRY F. MANBECK, JR.

*Attesting Officer*   *Commissioner of Patents and Trademarks*